United States Patent

Bielefeldt et al.

Patent Number: 5,283,378
Date of Patent: Feb. 1, 1994

[54] PROCESS FOR THE DECHLORINATION AND/OR DEBROMINATION OF FLUORINE-AND CHLORINE- AND/OR BROMINE-CONTAINING AROMATIC COMPOUNDS

[75] Inventors: Dietmar Bielefeldt, Ratingen; Albrecht Marhold, Leverkusen, both of Fed. Rep. of Germany

[73] Assignee: Bayer Aktiengesellschaft, Leverkusen, Fed. Rep. of Germany

[21] Appl. No.: 953,209

[22] Filed: Sep. 29, 1992

Related U.S. Application Data

[63] Continuation of Ser. No. 772,824, Oct. 8, 1991, abandoned.

[30] Foreign Application Priority Data

Oct. 18, 1990 [DE]  Fed. Rep. of Germany ....... 4033097

[51] Int. Cl.⁵ .............. C07C 25/13; C07C 25/18; C07C 17/24; C07C 17/34
[52] U.S. Cl. .................... 570/143; 570/144; 570/147; 570/176
[58] Field of Search ............. 570/143, 144, 147, 176

[56] References Cited

U.S. PATENT DOCUMENTS

| | | |
|---|---|---|
| 4,331,613 | 5/1982 | Marhold et al. |
| 4,827,057 | 5/1989 | Käsbauer et al. |
| 4,849,557 | 7/1989 | Kondo et al. |
| 4,885,415 | 12/1989 | Marhold et al. ............ 570/144 |
| 4,925,998 | 5/1990 | Abraham et al. |
| 4,962,246 | 10/1990 | Marhold et al. ............ 570/127 |
| 5,068,473 | 11/1991 | Kellner et al. ............ 570/176 |

FOREIGN PATENT DOCUMENTS

| | | |
|---|---|---|
| 0705056 | 3/1965 | Canada ............ 570/144 |
| 03013432 | 2/1989 | European Pat. Off. |
| 2928745 | 2/1981 | Fed. Rep. of Germany |
| 2615185 | 11/1988 | France |
| WO90/11987 | 10/1990 | PCT Int'l Appl. |
| 0296748 | 4/1971 | U.S.S.R. ............ 570/143 |

*Primary Examiner*—Marianne M. Cintins
*Assistant Examiner*—Michael B. Hydorn
*Attorney, Agent, or Firm*—Sprung Horn Kramer & Woods

[57] ABSTRACT

Fluorine- and chlorine- and/or bromine-containing aromatic compounds are dechlorinated and/or debrominated with hydrogen in an industrially advantageous and selective manner, if the palladium catalyst is present in stationary phase and the aromatic compound in gas phase.

5 Claims, No Drawings

PROCESS FOR THE DECHLORINATION AND/OR DEBROMINATION OF FLUORINE-AND CHLORINE- AND/OR BROMINE-CONTAINING AROMATIC COMPOUNDS

This application is a continuation of application Ser. No. 07/772,824, filed Oct. 8, 1991, now abandoned.

The present invention relates to an industrially particularly advantageous and selective process for the dechlorination and/or debromination of fluorine- and chlorine- and/or bromine-containing aromatic compounds.

It is known that aromatic compounds containing at least three fluorine atoms can be obtained by treating an aromatic compound containing at least three fluorine atoms and at least a further non-fluorine halogen atom with an acid and a finely divided metal powder (see British Patent Specification 1,067,412). When 1,3,5-trichloro-2,4,6-trifluorobenzene, acetic acid and zinc powder are used in this process, 91% of the feed material are recovered from the reaction product and only 8% of 1,3-dichloro-2,4,6-trifluorobenzene are obtained (see Example 6 of British Patent Specification 1,067,412).

Furthermore, the liquid phase hydrogenation of 2,6-dichloro-4-trifluoromethyl-3,5-difluorotoluene with hydrogen in the presence of palladium on carbon as the catalyst is known from German Offenlegungsschrift 3,909,213, Example 24, in which process the corresponding chlorine-free product 4-trifluoromethyl-3,5-difluorotoluene is obtained in 78% yield.

Finally, it is known from German offenlegungsschrift 2,928,745, Example 1, that a mixture of isomeric 1-chloro-trifluoromethylnaphthalenes can be converted in the liquid phase in methanol in 62.6% yield into trifluoromethylnaphthalene using Raney nickel as the catalyst.

In all these processes, the obtainable yield and selectivity of dechlorinated products is still unsatisfactory.

A process for the selective dechlorination and/or debromination of fluorine- and chlorine- and/or bromine-containing aromatic compounds with hydrogen in the presence of catalysts has now been found, which process is characterised in that the catalyst is present in stationary phase and the fluorine- and chlorine- and/or bromine-containing aromatic compound in mobile phase.

In the process according to the invention, it is possible to use, for example, fluorine- and chlorine- and/or bromine-containing aromatic compounds of the formula (1)

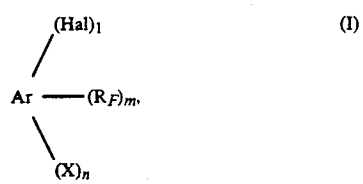

in which
Ar represents an aromatic radical having 6 to 10 C atoms,
Hal, independently of one another, represent chlorine or bromine,
$R_F$, independently of one another, represent fluorine or a fluorine-containing radical having 1 to 4 C atoms and 1 to 6 fluorine atoms,
X represents $C_1$- to $C_4$-alkyl, fluorinated $C_1$- to $C_4$-alkyl, $C_1$- to $C_4$-alkoxy, CHO, $CH_2OH$, CN, COO-$C_1$- to $C_4$-alkyl, $NH_2$, $CH_2NH_2$ or $NO_2$,
l represents 1, 2, 3 or 4,
m represents 1, 2, 3 or 4 and
n represents zero or 1,
where l+m+n corresponds to at least 2 and at most the number of possible valences on Ar.

Ar preferably represents phenyl or naphthyl, in particular phenyl.

Hal preferably represents chlorine.

$R_F$ preferably represents fluorine, $CF_3$, $CHF_2$, $CH_2F$, $CF_2CF_3$, $CH_2CF_3$, $CH_2CHF_2$, $CH_2CH_2F$, $OCF_3$, $OCF_2H$, $OCH_2F$, $OCF_2CF_2H$, $OCF_2CF_3$ or $N(CF_3)_2$.

If 2 or more $R_F$ radicals are present, they can be identical or different. 2 $R_F$ radicals can also together represent —O—$CF_2$—$CF_2$—O—, —O—$CF_2$—$CH_2$—O—, —O—$CF_2$—CHF—O— or —O—$CF_2$—O—.

X preferably represents $CH_3$, $CF_3$, $OCH_3$, $OCH_2CH_3$, CHO or CN.

l preferably represents 1 or 2, m preferably represents 1, 2 or 3.

If Ar represents phenyl, l+m+n is preferably 2, 3, 4, 5 or 6, in particular 3, 4 or 5. If Ar represents naphthyl, l+m+n is preferably 2, 3 or 4.

If Ar represents phenyl, it is furthermore preferred that at least one $R_F$ radical and at least one Hal radical are in the ortho or para position with respect to one another.

Based on one equivalent of chlorine and bromine atoms contained in the fluorine- and chlorine- and/or bromine-containing aromatic compound used in each case, for example, 1 to 50 mol of hydrogen can be used in the process according to the invention. This amount is preferably 2 to 20 mol.

For enabling the catalyst to be present during the process according to the invention in stationary phase, it is advantageously present in lumpy form. Supported catalysts containing transition metals as the catalytically active component are, for example, suitable. Preferred transition metals are palladium, platinum, nickel, cobalt, ruthenium, rhenium and rhodium, in particular palladium and platinum. Examples of support materials are activated carbons, aluminas, silicas, barium sulphate, spinels, silicates and titanium dioxide. Activated carbons and lithium/aluminium spinels are preferred. The catalysts can contain, for example, 0.1 to 50 g of transition metals per litre. This content is preferably 2 to 20 g/l.

Suitable pressures for the process according to the invention are, for example, those in the range from 0.1 to 20 bar.

The process according to the invention can be carried out, for example, at temperatures above 100° C., preferably at 120° C. to 400° C., in particular at 150° to 350° C.

An essential feature of the present invention is that the catalyst is present in stationary phase and the fluorine- and chlorine- and/or bromine-containing aromatic compound (=educt) in mobile phase, if appropriate together with the hydrogen and/or liquid or gaseous inert substances. For example, the catalyst can be in a solid bed in a reaction space, for example a tubular reactor, and the hydrogen can be passed through the catalyst bed in a mixture with the educt in gaseous form. The gas phase can contain inert gases, for example nitrogen, noble gases and/or vapours of inert solvents, for example vapours of toluene, xylene, methylcyclohexane, ligroin and/or petroleum ether.

If the gas phase contains inert gases, they are preferably solvent vapours. It is also possible to operate with a gas phase containing only the educt and hydrogen.

It is also possible to operate with a trickle phase, i.e. hydrogen in gaseous form is passed over a fixed-bed catalyst and the educt and/or any inert substances are in liquid phase passed through the catalyst bed completely or partially. The gas phase process in which all other components with the exception of the catalyst are passed through the reaction space in gaseous form is preferred.

The hydrogen which is preferably used is hydrogen of conventional technical grade, for example hydrogen having a purity of more than 80% by volume, preferably hydrogen having a purity of more than 95% by volume and particularly preferably hydrogen having a purity of more than 97% by volume. The impurities which can be present in the hydrogen in, for example, up to 20% by volume, preferably up to 5% by volume, particularly preferably up to 3% by volume, are nitrogen, methane, carbon dioxide and/or water vapour.

The flow rate of the mobile phase with respect to the stationary phase can be, for example, selected such that the resulting catalyst loads are in the range from 10 to 20,000 g of mobile phase per litre of catalyst and per hour. Catalyst loads in the range from 50 to 800 g of mobile phase per litre of catalyst and per hour are preferred.

The mixture present after the process according to the invention has been carried out can be worked up, for example, by cooling it, for example, to a temperature at which the dechlorinated and/or debrominated product substantially condenses, for example to a temperature in the range from 0° to 50° C. The then remaining gas phase can be subjected to alkaline washing, for example using sodium hydroxide solution, in order to remove the hydrogen halide contained therein. Excess hydrogen which then still remains in the gas phase can be recycled into the reactor. The condensed phase which has been separated off substantially contains the dechlorinated and/or debrominated product in technical grade purity, possibly together with the solvent used. In order to obtain pure products, the condensed phase can be taken up, for example, in an organic solvent, the solution can be washed with dilute sodium hydroxide solution and then subjected to fractional distillation.

In general, the reaction product of the process according to the invention does not contain or contains only very small amounts of aromatic compounds still containing chlorine or bromine. When compounds are used in the process according to the invention which contain several chlorine and/or bromine atoms, for example when compounds of the formula (I) are used where l is 2, 3 or 4, it is possible only in special cases to eliminate the chlorine and/or bromine atoms successively in stages.

It is possible that not only chlorine and/or bromine atoms are eliminated in the process according to the invention but also reactions with hydrogen take place on other parts of the molecule. When the aromatic compound used contains, for example, a CHO, CH$_2$OH, CH$_2$NH$_2$ or CN group, it is in general converted into a CH$_3$ group. In a corresponding manner, an NH$_2$ group is formed from an NO$_2$ group. Additional hydrogen consumption for reactions of this type must, if appropriate, be taken into account when metering in the hydrogen.

The process according to the invention makes it possible to prepare chlorine- and bromine-free aromatic compounds, in particular those of the formula (II)

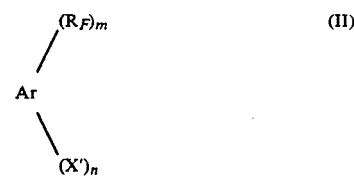

in which

Ar, R$_F$, m and n have the meaning given in formula (I),

X' represents C$_1$- to C$_4$-alkyl, fluorinated C$_1$- to C$_4$-alkyl, C$_1$- to C$_4$-alkoxy, COOC$_1$- to C$_4$-alkyl or NH$_2$, where m+n is at least 1 and at most corresponds to the number of possible valencies on Ar minus 1.

According to the invention, it is possible to obtain aromatic, fluorine-containing, but chlorine- and bromine-free compounds, in significantly improved selectivities and yields than in the known processes. In general, the conversions and selectivities are over 90% in the process according to the invention, and the conversions frequently over 95%. This is surprising for several reasons. For one, operation in the gas phase or in the trickle phase in general requires higher temperatures and higher temperatures in general mean a deterioration in the selectivity. On the other hand, in particular at higher temperatures, there is a risk of elimination of hydrogen fluoride and thus a risk of forming lower-fluorinated products. Finally, it is in principle also possible for the aromatic ring to be hydrogenated. Surprisingly, all this does not occur or only to a very minor extent.

The products preparable according to the invention can be used, for example, as intermediates for dyestuffs, plant protection agents and drugs. For example, 3-alkylbenzotrifluorides are important intermediates for diazo dyestuffs (see German Offenlegungsschrift 3,201,112).

EXAMPLES

General procedure

An upright heatable quartz tube with hydrogen inlet was filled with 200 ml of catalyst containing 0.5% by weight of palladium on activated carbon. The educt was metered in via a metering pump and the hydrogen was metered in via a rotameter. After the noble metal catalyst had been flushed and dried with nitrogen at atmospheric pressure, 0.2 to 0.25 mol per hour of the educt and 1 mol of hydrogen per chlorine atom of the educt were passed into the quartz tube at the temperature listed in the table. The hydrogen had a purity of more than 97%. This corresponded to a catalyst load of 210 to 250 g/l and per hour. Educts which are solid at room temperature were used in the form of 20 to 50% strength by weight solutions in toluene. The reaction mixture leaving the quartz tube was condensed at 0° to 20° C. The condensed portions were washed with water, dried over sodium sulphate and then analysed by gas chromatography. In some cases, the condensed portions were worked up after washing and drying by distillation.

In detail, the following reactions were carried out:

Example 1

1-Trifluoromethylnaphthalene was obtained at 210° C. from 1-trifluoromethyl-monochloronaphthalene (mixture of isomers) at a conversion of 100% and a selectivity of 94.6%.

Example 2

Bis(trifluoromethyl)naphthalene (mixture of isomers) was obtained at 210° C. from bis(trifluoromethyl)monochloronaphthalene (mixture of isomers) at a conversion of 98.3% and a selectivity of 93.8%.

Example 3

2,3-Difluoro-ethoxybenzene was obtained at 250° C. from 2,3-difluoro-6-chloro-ethoxybenzene at a conversion of 85.3% and a selectivity of 96.2%.

Example 4

3,4-Difluoro-trifluoromethylbenzene was obtained at 210° C. from 3,4-difluoro-5-chloro-trifluoromethylbenzene at a conversion of 99.0% and a selectivity of 98%.

Example 5

3,4-Difluoro-trifluoromethylbenzene was obtained at 230° C. from 3,4-difluoro-6-chloro-trifluoromethylbenzene at a conversion of 99.6% and a selectivity of 98.8%.

Example 6

2,3,4-Trifluoro-trifluoromethylbenzene was obtained at 200° C. from 2,3,4-trifluoro-5-chloro-trifluoromethylbenzene at a conversion of 98.9% and a selectivity of 91.2%.

Example 7

Trifluoromethoxybenzene was obtained at 230° C. from 2,4-dichloro-trifluoromethoxybenzene at a conversion of 100% and a selectivity of 91.4%.

Example 8

2-Trifluoromethyl-trifluoromethoxybenzene was obtained at 230° C. from 2,4-dichloro-6-trifluoromethyl-trifluoromethoxybenzene at a conversion of 100% and a selectivity of 92.2%.

Example 9

3-Trifluoromethyltoluene was obtained at 240° C. from 3-trifluoromethyl-4-chloro-toluene at a conversion of 99.4% and a selectivity of 98.1%.

Example 10

3-Trifluoromethyltoluene was obtained at 220° C. from 3-trifluoromethyl-4,6-dichlorotoluene using 10 mol of hydrogen per mole of educt at a conversion of 100% and a selectivity of 97.4%.

Example 11

1,3,5-Trifluorobenzene was obtained from 1,3,5-trifluoro-2,4,6-trichlorobenzene using 10 mol of hydrogen per mole of educt at a conversion of 100% and a selectivity of 93.8%.

Example 12

2,2,3,3-Tetrafluoro-1,4-benzodioxane was obtained at 210° C. from 6-bromo-2,2,3,3-tetrafluoro-1,4-benzodioxane at a conversion of 100% and a selectivity of 98.4%.

Example 13

5-Chloro-4-fluoro-2-trifluoromethylbenzaldehyde gave 4-fluoro-2-trifluoromethyltoluene at a selectivity of 72.4% and 5-chloro-4-fluoro-2-trifluoromethyltoluene at a selectivity of 16.3% at 210° C. and a conversion of 96.7%.

Example 14

3-Chloro-tetrafluorobenzonitrile was reacted at 240° C. The reaction products were collected in 300 ml of water and, after reaction was complete, the mixture was made alkaline with 40% strength by weight aqueous sodium hydroxide solution. The organic material was extracted with methyl tert.-butyl ether, analysed and then worked up by distillation. 2,3,4,6-Tetrafluoro-toluene of boiling point 108° C. was isolated in a yield of 77.3%.

Example 15

26.5 g of 4-chloro-3-amino-N,N-bistrifluoromethyl-aminobenzene were dissolved in 50 g of toluene and reacted at 350° C. The reaction products were introduced into 150 ml of water. The two-phase mixture obtained was made alkaline with 20% strength by weight aqueous sodium hydroxide solution, and the toluene phase was separated off, to give 10.3 g of 3-amino-N,N-bistrifluoromethyl-aminobenzene of boiling point 76° to 78° C. at 20 mbar by distillation.

Example 16

500 g of 3-chloro-4-trifluoromethoxy-toluene were reacted at 250° C. The reaction product was collected in a cooled receiver and the hydrogen chloride was passed into a neutralisation tank via a jacketed coil condenser. 4-Trifluoromethoxybenzene was isolated from the cooled receiver by distillation in a yield of 86.4%. The boiling point of the product was 129° to 131° C.

Example 17

Fluorobenzene was obtained at 200° C. from 4-fluorochlorobenzene at a conversion of 89% and a selectivity of 88%.

Example 18

The procedure of Example 17 was repeated, except that the catalyst used contained alumina as the support material. The conversion was in this case 100% and the selectivity 96.6%.

We claim:

1. Process for the selective dechlorination and/or debromination of a fluorine- and chlorine- and/or bromine-containing aromatic compound of the formula

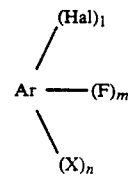

in which

Ar represents an aromatic radical having 6 to 10 C atoms,

Hal, independently of one another, represents chlorine or bromine,

X represents $C_1$- to $C_4$-alkyl, fluorinated $C_1$- to $C_4$-alkyl, $C_1$- to $C_4$-alkoxy, CHO, $CH_2OH$, CN, COO-$C_1$- to $C_4$-alkyl, $NH_2$, $CH_2NH_2$ or $NO_2$, l represents 1, 2, 3 or 4 m represents 1, 2, 3 or 4 and n represents zero or 1, where l+m+n corresponds to at least 2 and at most the number of possible valencies on Ar, with hydrogen in the presence of a supported catalyst containing palladium, wherein said catalyst is present in stationary phase and the fluorine- and chlorine- and/or bromine-containing compound and hydrogen are passed over said catalyst in gaseous phase.

2. The process of claim 1, wherein 1 to 50 mol of hydrogen are used per equivalent of chlorine and bromine atoms contained in said fluorine- and chlorine- and/or bromine-containing aromatic compound.

3. The process according to claim 1, wherein it is carried out at pressures in the range from 0.1 to 20 bar.

4. The process according to claim 1, wherein it is carried out at temperatures above 100° C.

5. The process according to claim 1, wherein the flow rate of the gas phase with respect to the stationary phase is selected such that the resulting catalyst loads are in the range from 10 to 20,000 g of gas phase per litre of catalyst and per hour.

* * * * *